(12) United States Patent
Holmes et al.

(10) Patent No.: US 10,898,725 B2
(45) Date of Patent: Jan. 26, 2021

(54) INTEGRATED OPTOGENETIC DEVICE WITH LIGHT-EMITTING DIODES AND GLASS-LIKE CARBON ELECTRODES

(71) Applicant: International Business Machines Corporation, Armonk, NY (US)

(72) Inventors: Steve Holmes, Ossining, NY (US); Stephen W. Bedell, Wappingers Falls, NY (US); Jia Chen, New York, NY (US); Hariklia Deligianni, Alpine, NJ (US); Devendra K. Sadana, Pleasantville, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 16/199,627

(22) Filed: Nov. 26, 2018

(65) Prior Publication Data
US 2020/0164222 A1 May 28, 2020

(51) Int. Cl.
*H01L 21/02* (2006.01)
*A61N 5/06* (2006.01)
(Continued)

(52) U.S. Cl.
CPC ........ *A61N 5/0622* (2013.01); *A61B 5/04001* (2013.01); *C30B 25/02* (2013.01);
(Continued)

(58) Field of Classification Search
CPC ........... H01L 21/0237; H01L 21/02491; H01L 21/0254; H01L 21/0262; H01L 21/02631
See application file for complete search history.

(56) References Cited

U.S. PATENT DOCUMENTS 6,566,218 B2    5/2003 Otani et al.
7,781,356 B2    8/2010 Kouvetakis et al.
(Continued)

FOREIGN PATENT DOCUMENTS

JP    2007250852 A    9/2007
JP    4756349          8/2011
JP    2013048200 A    3/2013

OTHER PUBLICATIONS

Kampasi, et al. "Fiberless multicolor neural optoelectrode for in vivo circuit analysis," Scientific Reports, 6:30961 | DOI: 10.1038/srep30961;Aug. 3, 2016, pp. 1-13.
(Continued)

*Primary Examiner* — Joseph M Galvin, III
(74) *Attorney, Agent, or Firm* — Cantor Colburn LLP; Jeffrey S LaBaw

(57) ABSTRACT

Embodiments of the invention are directed to an integrated optogenetic device. The integrated optogenetic includes a substrate layer having a first substrate region and a second substrate region. The device further includes a first contact formed over the substrate layer in the first substrate region and a second contact layer formed over the substrate layer in the second region. In addition, the device includes a light-emitting diode (LED) structure communicatively coupled to the first contact layer and a biosensor element communicatively coupled to the second contact layer. The first contact layer is configured to operate as a bottom contact that provides electrical contact to the LED structure. The first contact layer is further configured to be substantially lattice matched with the substrate layer and a bottom layer of the LED structure.

8 Claims, 20 Drawing Sheets

(51) Int. Cl.
*A61B 5/04* (2006.01)
*C30B 25/02* (2006.01)

(52) U.S. Cl.
CPC ...... *H01L 21/0237* (2013.01); *H01L 21/0254* (2013.01); *H01L 21/0262* (2013.01); *H01L 21/02491* (2013.01); *H01L 21/02631* (2013.01)

(56) References Cited

U.S. PATENT DOCUMENTS

| | | | | |
|---|---|---|---|---|
| 2006/0236923 | A1* | 10/2006 | Kouvetakis | H01L 21/02439 117/108 |
| 2011/0155586 | A1* | 6/2011 | Elibol | G01N 27/3278 205/777.5 |
| 2011/0220895 | A1* | 9/2011 | Hirai | H01L 29/7869 257/57 |
| 2013/0030274 | A1* | 1/2013 | Jamieson | A61N 5/0622 600/377 |
| 2013/0334563 | A1 | 12/2013 | Lei et al. | |
| 2016/0066789 | A1 | 3/2016 | Rogers et al. | |
| 2016/0287113 | A1* | 10/2016 | Hebert | A61B 5/04001 |
| 2018/0193663 | A1* | 7/2018 | Deligianni | A61N 5/0622 |

OTHER PUBLICATIONS

Seymour, et al., "State-of-the-art MEMS and microsystem tools for brain research," Microsystems & Nanoengineering (2017) 3, 16066; doi:10.1038/micronano.2016.66; Jan. 2, 2017, pp. 1-16.

Wu, et al., "Monolithically Integrated µLEDs on Silicon Neural Probes for High-Resolution Optogenetic Studies in Behaving Animals," Neuron. Dec. 16, 2015; 88(6): 1136-1148. doi:10.1016/j.neuron.2015.10.032; pp. 1-26.

* cited by examiner

INTEGRATED OPTOGENETIC DEVICE WITH LIGHT-EMITTING DIODES AND GLASS-LIKE CARBON ELECTRODES

BACKGROUND

The present invention generally relates to fabrication methods and resulting structures for semiconductor devices. More specifically, the present invention relates to fabrication methods and resulting structures for an integrated optogenetic device with light-emitting diodes (LEDs) and glass-like carbon electrodes.

Optogenetics revolutionized neural circuit analysis by introducing photosensitive proteins (opsins) into specific cell types so that these cells can respond to an optical stimulus with defined action potential patterns. Using appropriate wavelengths to target a particular opsin, cell-type specificity can be achieved with well-controlled temporal resolution. Therefore, a spike timing during specific neural computations and behaviors at the temporal resolution of a few milliseconds in the intact brain can be tested.

When the optical stimulus is achieved via, for example, light-emitting diodes (LEDs), the neural computations and recordings can be performed by an analytical device, such as a biosensor. An example of a biosensor is an electrode that is configured to generate an electrical current based on a detection or measurement of one or more chemical component. Glass-like carbon is considered an optimal material for forming the electrodes used in biosensors.

SUMMARY

Embodiments of the invention are directed to an integrated optogenetic device. A non-limiting example of the integrated optogenetic device includes a substrate layer with a first substrate region and a second substrate region. The device further includes a first contact formed over the substrate layer in the first substrate region and a second contact layer formed over the substrate layer in the second region. In addition, the device includes a light-emitting diode (LED) structure communicatively coupled to the first contact layer and a biosensor element communicatively coupled to the second contact layer. The first contact layer is configured to operate as a bottom contact that provides electrical contact to the LED structure. The first contact layer is further configured to be substantially lattice matched with the substrate layer and a bottom layer of the LED structure.

Further, embodiments of the present invention are directed to a method of forming an integrated optogenetic device. A non-limiting example, the method includes forming a substrate layer with a first substrate region and a second substrate region. The method further includes forming a first contact layer over the substrate layer in the first substrate region and a second contact layer over the substrate layer in the second substrate region. In addition, the method includes forming a light-emitting diode (LED) structure communicatively coupled to the first contact layer and a biosensor element communicatively coupled to the second contact layer. The first contact layer is configured to operate as a bottom contact that provides electrical contact to the LED structure. The first contact layer is further configured to be substantially lattice matched with the substrate layer and a bottom layer of the LED structure.

Even further, embodiments of the invention are directed to a method of using an integrated optogenetic device. A non-limiting example of the method includes accessing a sample of fluid. The method further includes stimulating the sample of fluid by a light-emitting diode (LED) structure of the integrated optogenetic device and exposing the stimulated sample of fluid to a biosensor element of the integrated optogenetic device. Based on the biosensor element contacting the stimulated material in the extracellular fluid, the integrated optogenetic device generates a measurement. Based on the measurement, a computer processor of the integrated optogenetic device generates an output that is proportional to predetermined characteristics. The integrated optogenetic device includes a substrate layer with a first substrate region and a second substrate region. The device further includes a first contact formed over the substrate layer in the first substrate region and a second contact layer formed over the substrate layer in the second region. In addition, the device includes the (LED) structure communicatively coupled to the first contact layer and the biosensor element communicatively coupled to the second contact layer. The first contact layer is configured to operate as a bottom contact that provides electrical contact to the LED structure. The first contact layer is further configured to be substantially lattice matched with the substrate layer and a bottom layer of the LED structure.

Additional technical features and benefits are realized through the techniques of the present invention. Embodiments and aspects of the invention are described in detail herein and are considered a part of the claimed subject matter. For a better understanding, refer to the detailed description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the embodiments of the invention are apparent from the following detailed description taken in conjunction with the accompanying drawings in which:

Figure 1:
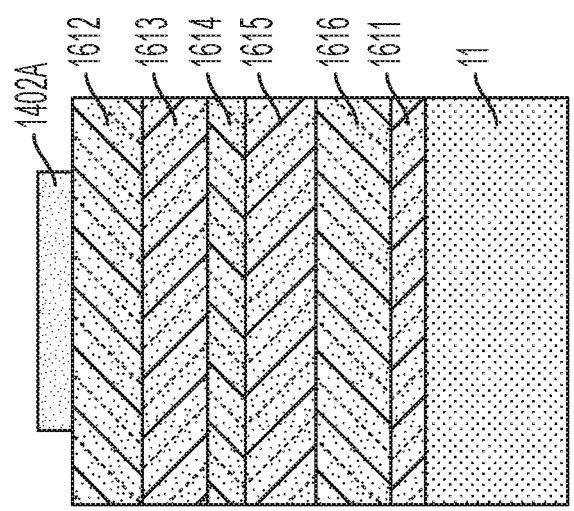
FIG. 1 depicts a multilayer stack used to form an LED in accordance with embodiments of the invention.

In the accompanying figures and following detailed description of the described embodiments, the various elements illustrated in the figures are provided with two, three or four digit reference numbers. With minor exceptions, the leftmost digit(s) of each reference number correspond to the figure in which its element is first illustrated.

DETAILED DESCRIPTION

For the sake of brevity, conventional techniques related to semiconductor device and integrated circuit (IC) fabrication may or may not be described in detail herein. Moreover, the various tasks and process steps described herein can be incorporated into a more comprehensive procedure or process having additional steps or functionality not described in detail herein. In particular, various steps in the manufacture of semiconductor devices and semiconductor-based ICs are well known and so, in the interest of brevity, many conventional steps will only be mentioned briefly herein or will be omitted entirely without providing the well-known process details.

Turning now to an overview of technologies that are more specifically relevant to aspects of the invention, optogenetics is a technique that uses light to modulate membrane voltage in cells, such as neural cells, in body tissue. The light can be used to trigger changes in proteins that control membrane potentials in the cells through excitatory or inhibitory membrane currents. This ability to control cell activities has proven instrumental in preclinical studies and holds significant potential for the treatment of diseases such as Parkinson's, epilepsy, chronic pain, addiction, and depression, among others. Optogenetic devices are used to control cells in living tissue, for example, neurons, that have been genetically modified to express light-sensitive ion channels. More specifically, in optogenetics, neuromodulation methods are used to control and monitor the activities of individual neurons in living tissue and to precisely measure these manipulation effects in real-time. Light-emitting diodes (LEDs) have been used in the optogenetic devices as a light source to facilitate neural stimulations.

As used herein, an LED is a semiconductor device that emits light when an electric current is passed through it. Light is produced when the particles that carry the current (known as electrons and holes) combine within the semiconductor material. Inside the semiconductor material of the LED, the electrons and holes are contained within energy bands. The separation of the bands (i.e., the bandgap) determines the energy of the photons that are emitted by the LED. The photon energy determines the wavelength of the emitted light, and hence its color. Different semiconductor materials with different bandgaps produce different colors of light. The precise wavelength (color) can be tuned by altering the composition of the light-emitting, or active, region. LEDs can be formed from compound semiconductor materials, which are made up of elements from group III and group V of the periodic table (these are known as III-V materials). Examples of III-V materials commonly used to make LEDs are gallium arsenide (GaAs), gallium phosphide (GaP) and gallium nitride (GaN). The main semiconductor materials used in LEDs include indium gallium nitride (InGaN), which is responsible for blue, green and ultraviolet high-brightness LEDs; aluminum gallium indium phosphide (AlGaInP), which is responsible for yellow, orange and red high-brightness LEDs; aluminum gallium arsenide (AlGaAs), which is responsible for red and infrared LEDs; and gallium phosphide (GaP), which is responsible for yellow and green LEDs. Different color LEDs can activate/deactivate different neural circuits and influence the resulting release of neurochemicals. In embodiments of the invention, the LEDs can be formed on a transparent dielectric substrate to facilitate passing light to and from the LEDs in order to obtain optical-based measurements (e.g., optogenetic measurements).

Group III nitride materials have been used to fabricate the LEDs. Group III nitride materials include GaN, AN, InN and their alloys such as AlGaN, InGaN, and AlInGaN. These materials are semiconductor compounds that have a wide direct bandgap, which permits highly energetic electronic transitions to occur. Such electronic transitions can result in group III nitride materials having a number of important properties, including the ability to efficiently emit blue and ultraviolet light, the ability to transmit signals at high frequency, and others. These properties of group III nitride materials make them well-suited for uses in optogenetic devices.

However, semiconductor structures having group III nitrides formed on silicon substrates have presented significant drawbacks. Such structures have been complicated and expensive to fabricate. Moreover, light emitting optoelectronic devices having group III nitrides formed on silicon substrates are less efficient than such devices formed on sapphire substrates. In optoelectronic applications, silicone is approximately 45% absorbing in the ultraviolet (UV) region, while sapphire is totally transparent. Thus, a light-emitting optoelectronic device (e.g., optogenetic device) based on group III nitrides will be less efficient if silicone is used as a substrate than if sapphire is used as a substrate.

The growth of group III nitrides, including GaN, is commonly accomplished by heteroepitaxy using methods of metalorganic chemical vapor deposition (MOCVD) and molecular beam epitaxy (MBE). However, GaN has a lattice mismatch with sapphire of about 16%. Coupled with mismatches in thermal expansion coefficients, the misfit dislocations produced in GaN during heteroepitaxial growth pose a limitation to the ultimate performance of nitride-based electronics. Various growth schemes involving patterned substrates have been developed to improve the dislocation density. The resulting semiconductor devices, however, often develop cracks and other undesirable morphologies.

As previously noted herein, glass-like carbon is considered an optimal material for forming the electrodes used in biosensors. Typically, a biosensor element formed from glass-like carbon can be fabricated by using known semiconductor fabrication processes (e.g., spin coating, chemical vapor deposition, lithographic patterning, etching, etc.) to deposit a layer of a glass-like carbon precursor (e.g., a carbon-rich polymer applied as an organic planarization layer (OPL)) on a substrate carrier, and then applying a high temperature anneal (e.g., about 900 Celsius degrees to about 1200 Celsius degrees) to convert the glass-like carbon precursor to a layer of glass-like carbon material. The layer of glass-like carbon material can be patterned and etched to form one or more pillars of the biosensor element. The above-described high temperature anneal can cause volume shrinkage (e.g., from about 30% to about 50%) in the resulting glass-like carbon material, which can result in some delamination of the glass-like carbon electrodes.

Turning now to an overview of aspects of the invention, embodiments of the invention provide semiconductor structures (e.g., LEDs) with group III nitride materials formed on a sapphire substrate, wherein the semiconductor structures are devoid of the drawbacks described above. A biosensor element in accordance with aspects of the present invention includes a biological sensitive recognition element (e.g., antibodies, nucleic acids, enzymes, or aptamers) placed on a physicochemical transducer and connected to a detector to identify the presence, concentrations and/or kinetics of one or more specific analytes in a sample. The biosensor element is formed from glass-like carbon electrodes. The glass-like carbon electrode can function as both the recognition element and the transducer. Glass-like carbon is considered an optimal material for forming the electrodes used in biosensing devices. Glass-like carbon is a non-graphitizing carbon that combines glassy and ceramic properties with those of graphite. The useful properties of glass-like carbon in biosensor applications can include high temperature resistance, hardness (e.g., 7 Mohs), low density, low electrical resistance, low friction, low thermal resistance, extreme resistance to chemical attack and impermeability to gases and liquids. The glass-like carbon are excellent catalysts for the adsorption and electro-oxidation of neurochemicals.

An integrated optogenetic device according to embodiments of the invention avoids the previously-described high temperature anneals having a negative impact on the glass-like carbon electrodes by providing a stable structure that results from the fabrication methods described herein, including providing a near lattice-matched template for the growth of active layers.

In embodiments of the invention, an integrated optogenetic device with a light-emitting diode (LED) and a biosensor element is provided that allows for stimulation (e.g., neural stimulation) at the electrode-tissue interface and for recording the neural response and the resulting neurochemical release of, for example, dopamine, serotonin, adenosine, DOPAC, and/or glutamate. Embodiments of the present invention provide fabrication and resulting structure for an integrated optogenetic device with LEDs and glass-like carbon electrodes as the biosensor element. More specifically, embodiments of the invention provide a self-contained and integrated optogenetic sensing system by forming LEDs along with glass-like carbon electrodes on the sapphire substrate with $ZrB_2$ buffer layer. The integrated optogenetic device is capable of both activating neurons using the LEDs and recording neural electrical activity and the resulting neurochemistry in the extracellular or intracellular neuronal space. For example, the integrated optogenetic device can electrochemically record neurotransmitters, such as dopamine, serotonin, adenosine, DOPAC and other neurochemicals.

In embodiments of the invention, a substrate layer formed from zirconium diboride ($ZrB_2$) can be provided over the sapphire substrate. $ZrB_2$ provides an electrically conductive lattice-matched substrate for GaN growth. $ZrB_2$ has a hexagonal structure with lattice constants a=3.169 Å and c=3.530 Å. The in-plane lattice constant has only 0.6% mismatch with that of GaN (a=3.189 Å). The thermal expansion coefficients along [1010] on the basal plane are also well-matched between $ZrB_2$ and GaN, being 5.9×10-6 K-1 and 5.6×10-6 K-1, respectively.

An integrated optogenetic device embodying aspects of the invention can include a plurality of LEDs, e.g., GaN-based LEDs with a plurality of other color LEDs. In order to fabricate high performance GaN based devices, GaN patterning (i.e., etching) techniques are important. A plasma based dry etch and a chemical based wet etch are the two major etch techniques for GaN patterning.

An integrated optogenetic device in accordance with aspects of the invention can be provided with a housing. After completion of device fabrication processes in accordance with aspects of the invention, a wafer having formed thereon integrated optogenetic device in accordance with aspects of the invention are separated into micro-chips (i.e., chips), and the final products are packaged. IC packaging typically involves encasing the silicon chip(s) inside a hermetically sealed plastic, metal or ceramic package that prevents the chip(s) from being damaged by exposure to dust, moisture or contact with other objects.

In embodiments of the invention, the housing is formed from bio-compatible material to facilitate in vivo testing using the integrated optogenetic device 100. The housing can also include a network of microfluidic channels (not shown) for opsin pumping/delivery, which is used in optogenetics testing.

In embodiments of the invention, an interconnect network is provided and includes conductive interconnect layers that form a network of pathways that transport signals throughout the integrated optogenetic device, thereby connecting circuit components of the device. Interconnect layers are themselves interconnected by a network of contact points formed through the wafers of the IC. For example, a through-silicon via (TSV) is an electrical contact point that passes completely through the semiconductor wafer or die.

In embodiments of the invention, a fractal antenna can be used to provide wireless communications into and out of the integrated optogenetic device. A fractal antenna is an antenna that uses a fractal, self-similar design to maximize the length, or increase the perimeter (on inside sections or the outer structure), of material that can receive or transmit electromagnetic radiation within a given total surface area or volume. In embodiments of the invention, the fractal antenna can be implemented as an inductive circuit. In embodiments of the invention, the fractal antenna can be secured to the inside/outside of the housing. In some embodiments of the invention, a fractal antenna can be provided inside the IC housing in/on one of the substrates of the integrated optogenetic device.

Figure 18:
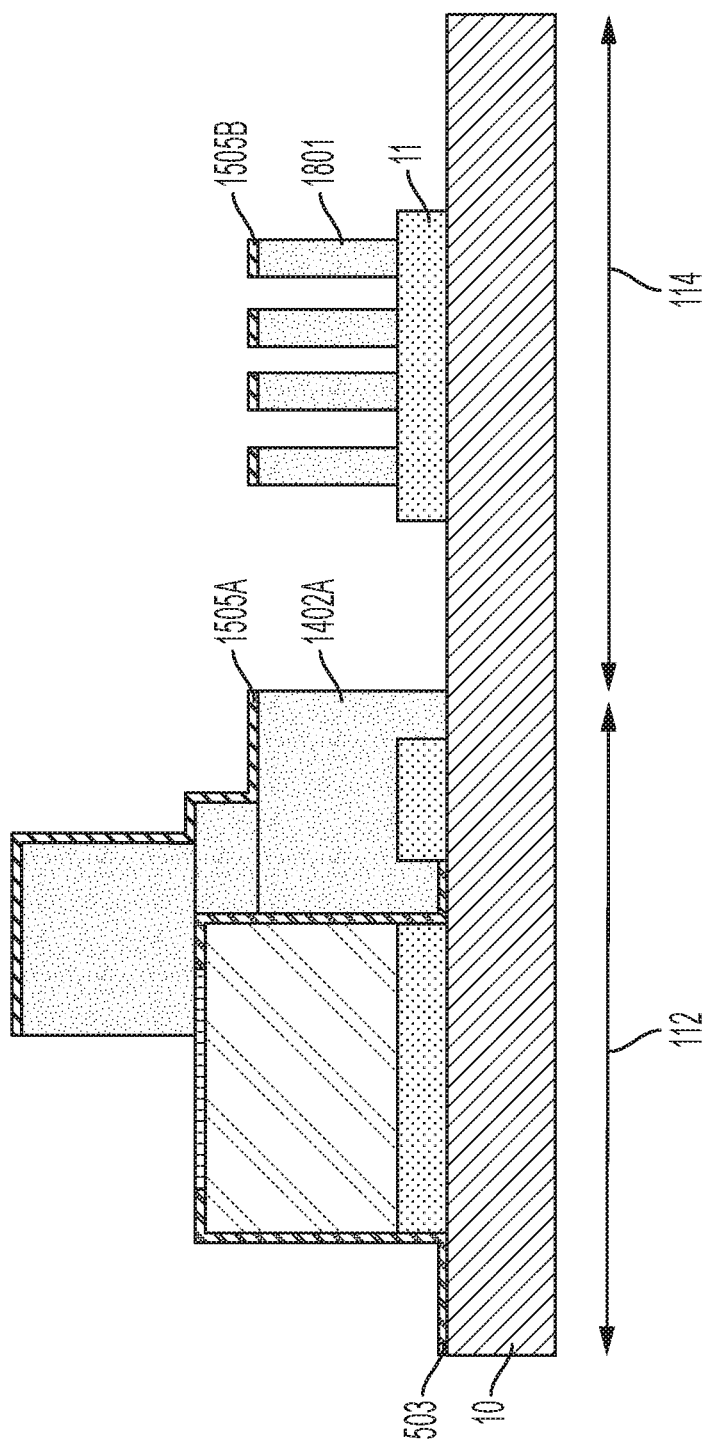
FIG. 18 depicts a cross-sectional view of the integrated optogenetic device after a fabrication stage in accordance with embodiments of the invention.
Figure 19:
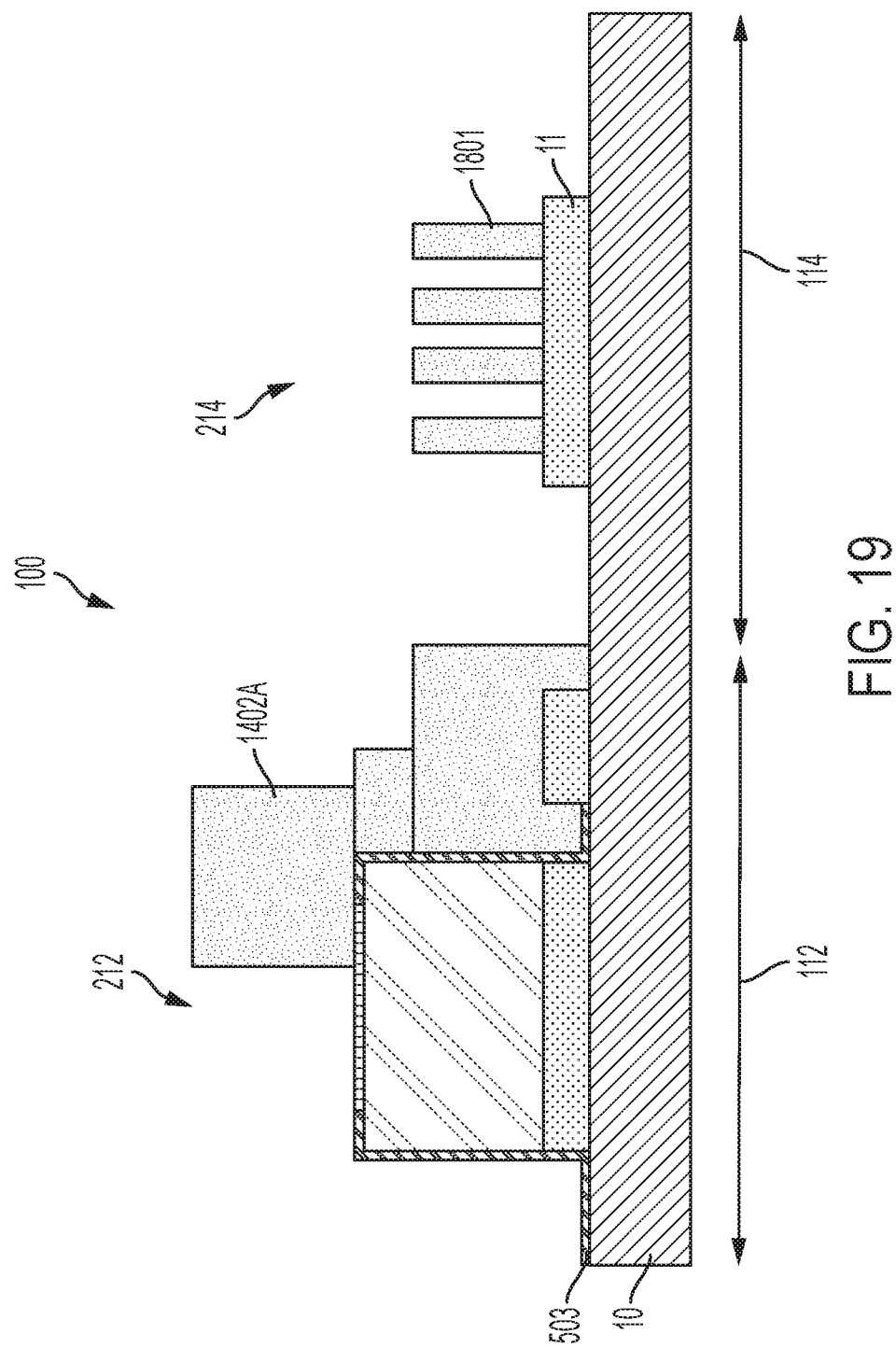
FIG. 19 depicts a cross-sectional view of the integrated optogenetic device after a fabrication stage in accordance with embodiments of the invention.

Turning now to a more detailed description of aspects of the present invention, FIGS. 2-19 illustrate an exemplary method for forming an integrated optogenetic device 100 illustrated on FIG. 19. Referring initially to FIG. 19, the integrated optogenetics device 100 includes a substrate layer 10, which includes a first substrate region 112 and a second substrate region 114. A light-emitting diode (LED) structure 212 is formed over the substrate layer 10 in the first substrate region 112, and a biosensor element 214 is formed over the substrate layer 10 in the second substrate region 114.

Referring now to FIG. 1, in embodiments of the invention, the LED structure 212 includes an active multilayer stack 16 formed over a buffer and contact (BAC) layer 11 in the first substrate region 112. The active multilayer stack 16 can be formed of gallium nitride (GaN), aluminum nitride (AlN), indium nitride (InN) or any of their alloys including aluminum gallium nitride (AlGaN), indium gallium nitride (InGaN), and aluminum indium gallium nitride (AlInGaN). More specifically, the active multilayer stack 16 can include a GaN buffer layer 1611, an n-type GaN layer 1616, an n-type AlGaN layer 1615, InGaN as a third (emission) layer 1614, a p-type AlGaN layer 1613, and a p-type GaN layer 1612. The p-type GaN layer 1612 is in a contrast to the n-type GaN layer 1616. Electrons are drifted by an external voltage in the n-type GaN layer 1616, while holes are drifted by the external voltage in the p-type GaN layer 1612. Therefore, the holes and the electrons are mutually recombined in a metal top layer described below, thereby emitting light. The BAC layer 11 provides a bottom electrical contact to the active multilayer stack 16, as well as a buffering function that is, in effect, a lattice match interface between the substrate 10 and the active multilayer stack 16. A glassy-carbon region 1402A functions as a top contact of the active multilayer stack 16.

In embodiments of the invention, the biosensor element 214 shown in FIG. 19 includes a pillar-shaped electrode body 1801. In embodiments of the invention, the term "pillar-shaped" refers to an elongated structure that is taller than it is wide. In embodiments of the invention, the pillar-shaped electrode body 1801 is formed of a glass-like carbon material. While FIGS. 2-19 illustrate that the first substrate region 112 is adjoining the second substrate region 114, a person skilled in the art would understand that this configuration is not required, and other configurations are possible.

Figure 2:
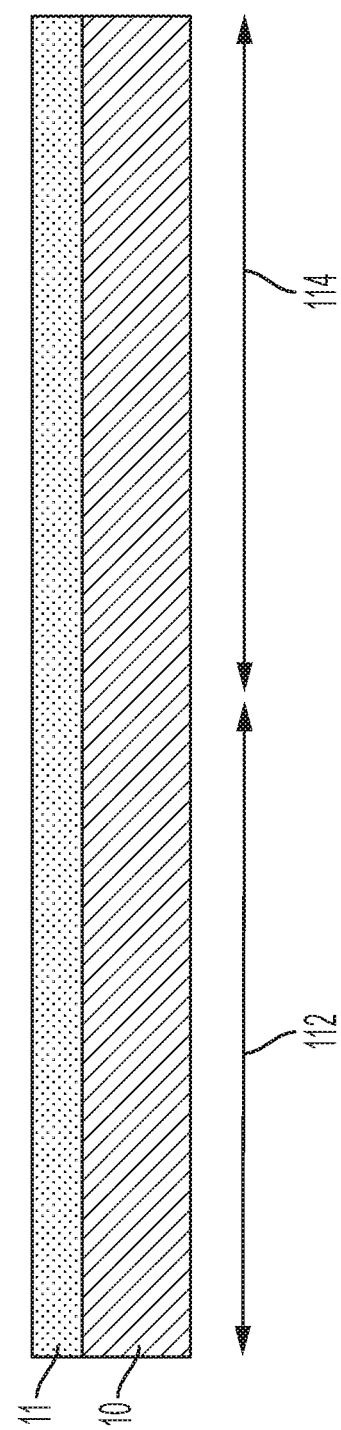
FIG. 2 depicts a cross-sectional view of an integrated optogenetic device after an initial fabrication stage in accordance with embodiments of the invention.

FIG. 2 depicts a cross-sectional view of the integrated optogenetics device 100 after an initial fabrication stage according to embodiments of the invention. In the fabrication stage as shown in FIG. 2, a second substrate layers 11 (i.e., a contact layer) is formed over the substrate layer 10. In embodiments of the invention, the substrate layer 10 can be a bulk substrate of semiconductor material, for example, silicon (Si), silicon carbide ($\alpha$-SiC), and sapphire ($Al_2O_3$). In addition, multiple layers of the semiconductor materials can be used as the second substrate layer, 11, depending on applications of the integrated optogenetics device 100. According to embodiments of the invention, the second substrate layer 11 is preferably composed of $ZrB_2$. In addition, the second substrate layers 11 can be of any diboride material having the formula $XB_2$, where X is an element selected from the group consisting of Zr and Ti.

The second substrate layer 11 is formed over the substrate layer 10 by epitaxy. In embodiments of the invention, deposition of the second substrate layer 11 is achieved by using gas-source molecular beam epitaxy (GSMBE), which includes a flux of a gaseous precursor directed onto a substrate under conditions where the precursor reacts with the substrate to commence growth of epitaxial reflective thin film on the substrate. It will be understood that other known processes for growing epitaxial films can be used. For example, the $ZrB_2$ layer also could be grown by chemical vapor deposition (CVD) using a heavily diluted zirconium borohydride gas source. The dilution agent can be hydrogen or any inert gas, such as helium, argon or nitrogen.

According to embodiments of the present invention, the second substrate layer 11 provides a near lattice-matched template for the growth of the active multilayer stack 16 composed of epitaxial group III nitrides formed over the second substrate layer 11, as described further below in FIG. 2. The second substrate layer 11 has a thickness of about 25 nm to about 100 nm. A typical $ZrB_2$ substrate layer with a thickness of 25 nm has a metallic appearance and is 100% reflecting in the visible to ultraviolet (UV) wavelength range. Accordingly, when the second substrate layer 11 is composed of $ZrB_2$, the second substrate layer 11 can function as a lower contact for the LED structure 212 and the biosensor element 214 with the glassy carbon electrodes.

Figure 3:
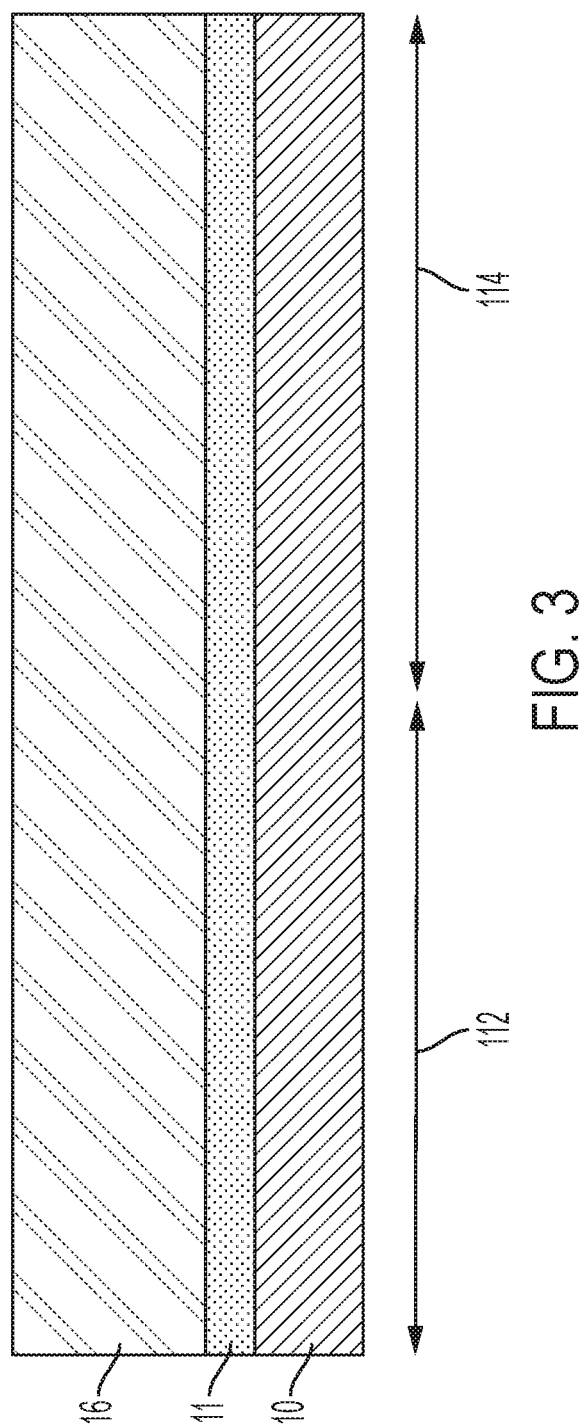
FIG. 3 depicts a cross-sectional view of the integrated optogenetic device after a fabrication stage in accordance with embodiments of the invention.

FIG. 3 illustrates the active multilayer stack 16 formed over the second substrate layer 11 by epitaxy. The active multilayer stack 16 is described in more detail in FIG. 1.

The growing processes of the active multilayer stack 16 are typically metal organic chemical vapor deposition (MOCVD) or molecular beam epitaxy (MBE) techniques. These processes are normally run under conditions which are as near as possible to stoichiometry. In order to form the active multilayer stack 16 on the sapphire substrate (i.e., the substrate layers 10) as described above, a metal organic chemical vapor deposition (MOCVD) is generally used. The MOCVD process involves introducing different source gases into an environment (e.g., a process system) around a substrate and providing conditions that promote a reaction between the gases to form a layer on the substrate surface. The reaction proceeds until a layer of desired thickness is achieved. The composition of the layer can be controlled, as described further below, by several factors including gas composition, gas concentration, and the reaction conditions (e.g. temperature and pressure).

According to embodiments of the invention, the LED structure 212 and the biosensor element 214 can be formed using pattern etching material processing methodologies. Pattern etching involves the application of a thin layer of light-sensitive material, such as photo-resist, to an upper surface of a substrate material (e.g., the post-anneal glass-like carbon) that is subsequently patterned in order to provide a mask for transferring this pattern to the underlying thin layer of light sensitive material on the substrate during etching. The patterning of the light-sensitive material generally involves exposure by a radiation source through a reticle (and associated optics) of the light-sensitive material using, for example, a photo-lithography system, followed by the removal of the irradiated regions of the light-sensitive material (as in the case of positive photo-resist), or non-irradiated regions (as in the case of negative resist) using a developing solvent.

In embodiments of the invention, a mask layer can include multiple sub-layers. By utilizing a multi-layer mask, the top mask layer, which includes the light-sensitive material as described above, can be thinner and, therefore, a smaller feature size can be achieved using conventional photo-lithography techniques. In order to generate a mask layer of sufficient thickness for the ensuing primary etch process, additional material layers can be formed underlying the top mask layer. The pattern, formed in the top mask layer using lithographic techniques, is transferred to the underlying layer or layers that include the mask layer for the primary etch process.

Figure 4:
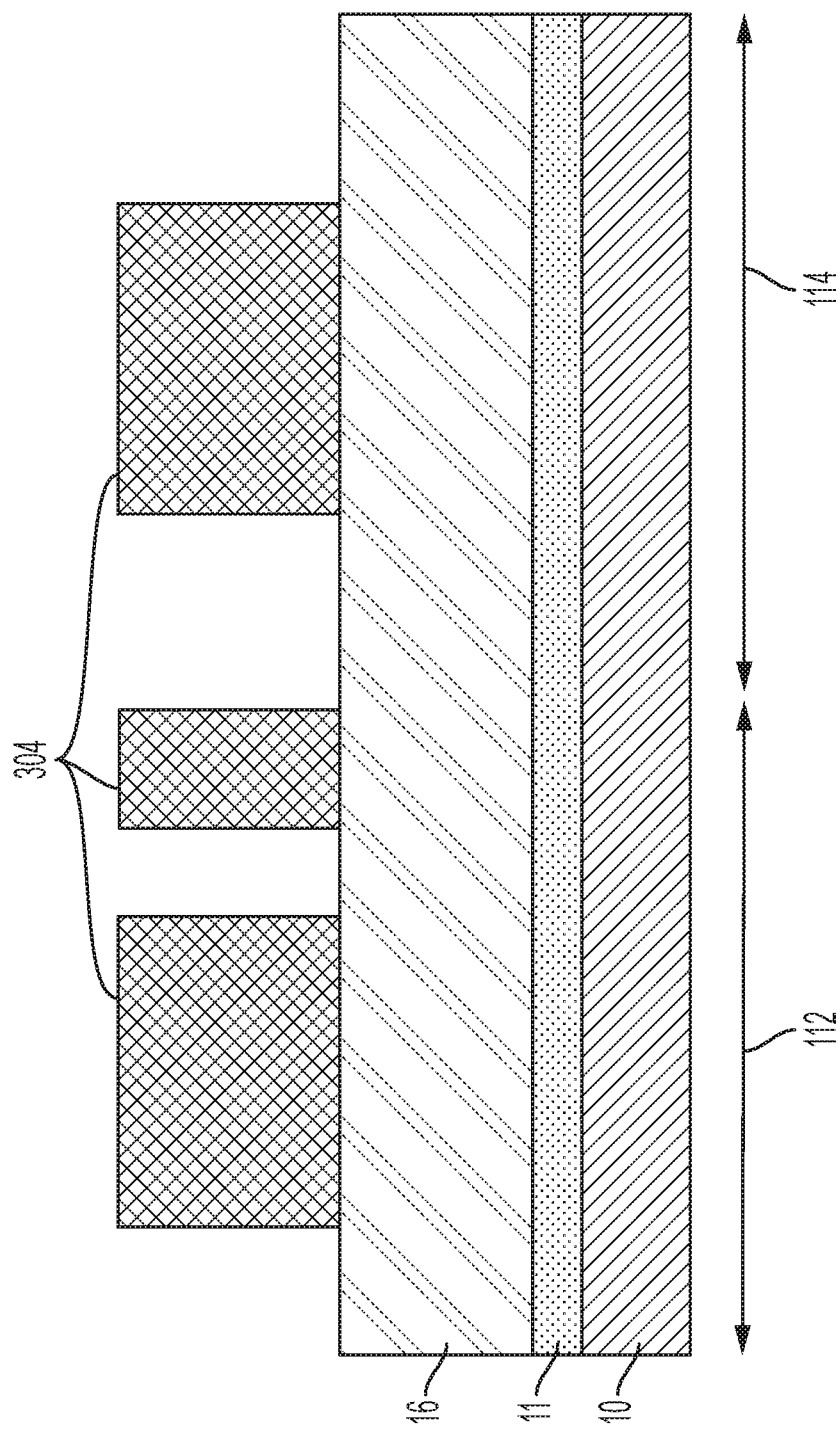
FIG. 4 depicts a cross-sectional view of the integrated optogenetic device after a fabrication stage in accordance with embodiments of the invention.

In FIG. 4, a photo resist 304 has been deposited for defining the first substrate region 112, the second substrate region 114, and an interconnect network (not shown) including a wire network and pads.

Figure 5:
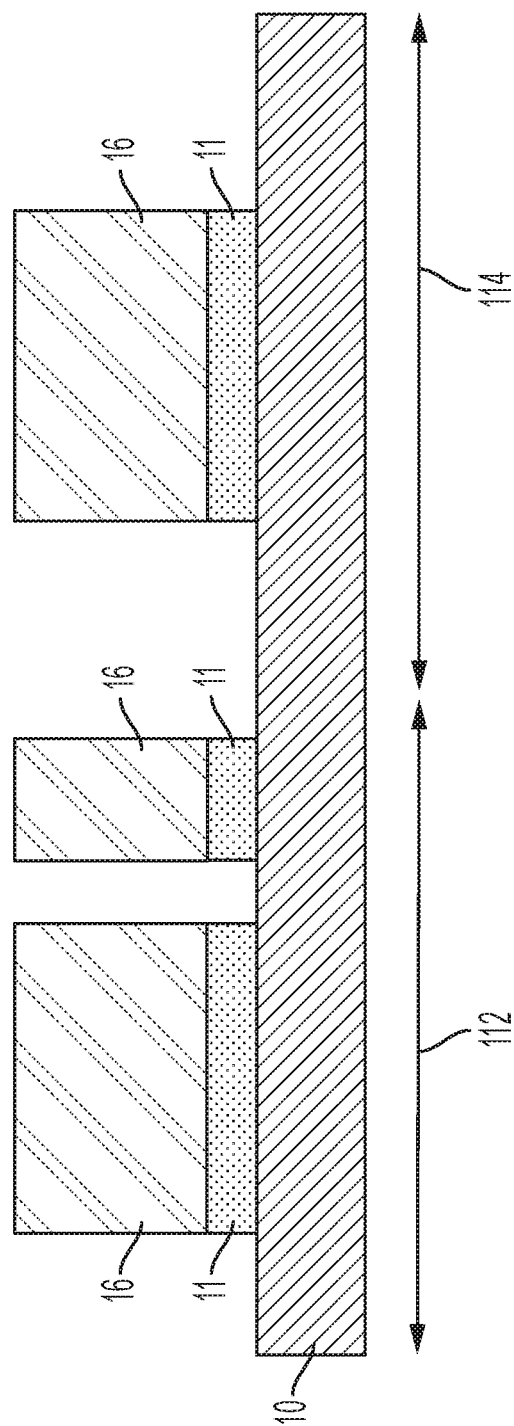
FIG. 5 depicts a cross-sectional view of the integrated optogenetic device after a fabrication stage in accordance with embodiments of the invention.

In FIG. 5, etching has been performed for forming the LED structure 212 and the biosensor element 214 (shown in FIG. 19). The resist 304 has been dissolved and removed.

Figure 6:
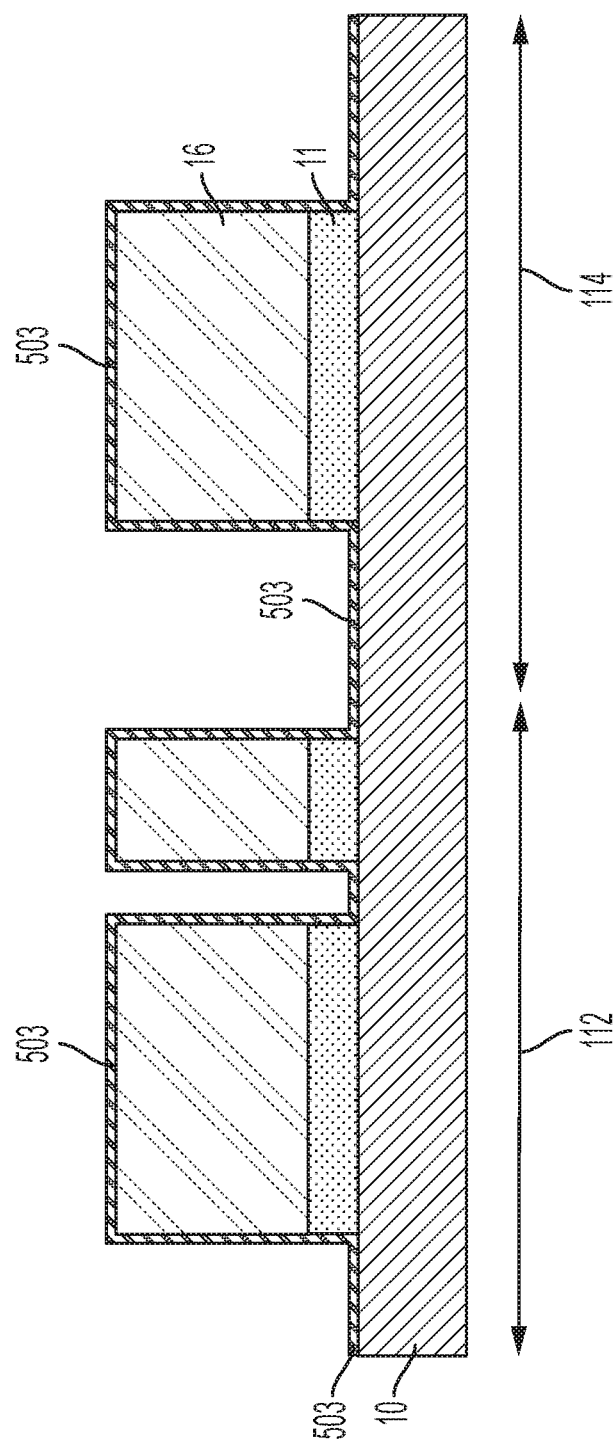
FIG. 6 depicts a cross-sectional view of the integrated optogenetic device after a fabrication stage in accordance with embodiments of the invention.

In FIG. 6, a dielectric 503 (e.g., $Al_2O_3$) is deposited using conventional fabrication techniques. In embodiments of the invention, the dielectric 503 can be deposited using a spin coating technique.

Figure 7:
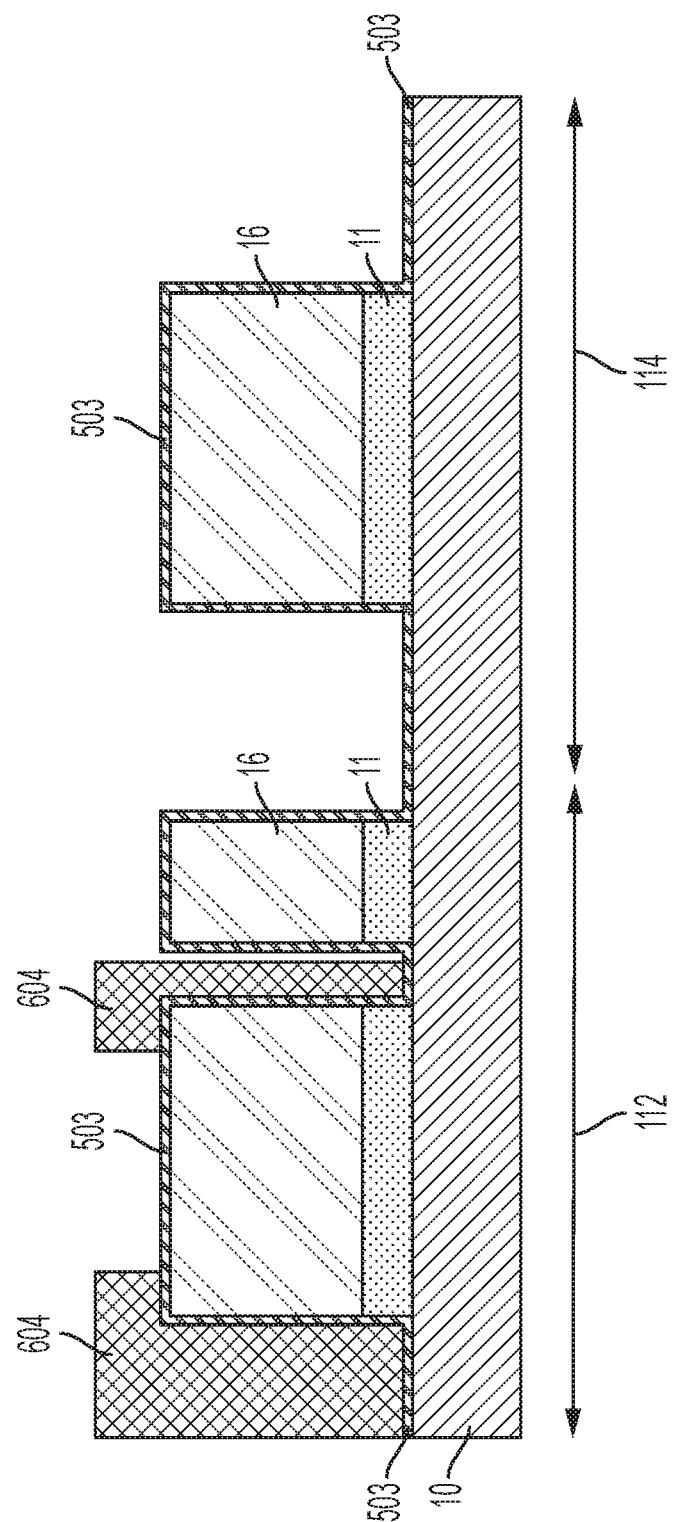
FIG. 7 depicts a cross-sectional view of the integrated optogenetic device after a fabrication stage in accordance with embodiments of the invention.

In FIG. 7, a photo resist pattern 604 is deposited. The resist pattern 102 defines an area of the dielectric 503.

Figure 8:
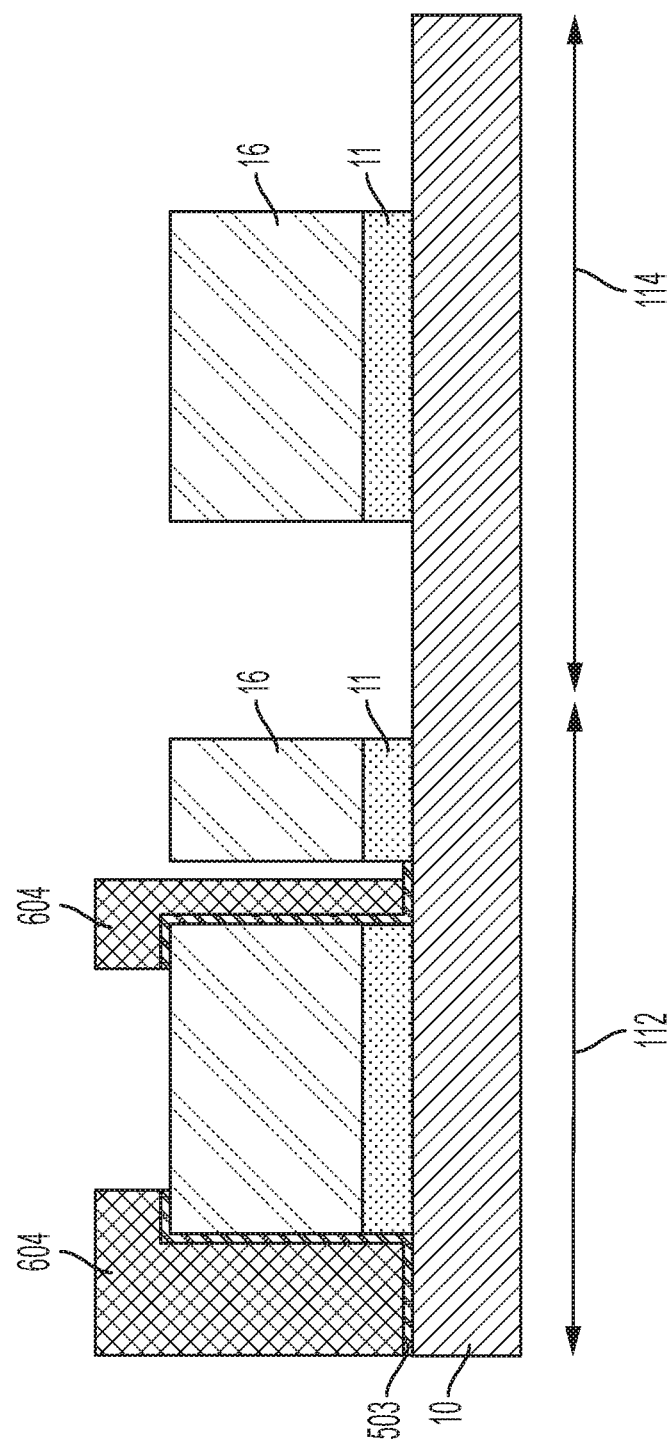
FIG. 8 depicts a cross-sectional view of the integrated optogenetic device after a fabrication stage in accordance with embodiments of the invention.

In FIG. 8, the area of the dielectric 503 has been removed using a dilute hydrofluoric acid (DHF) processes.

Figure 9:
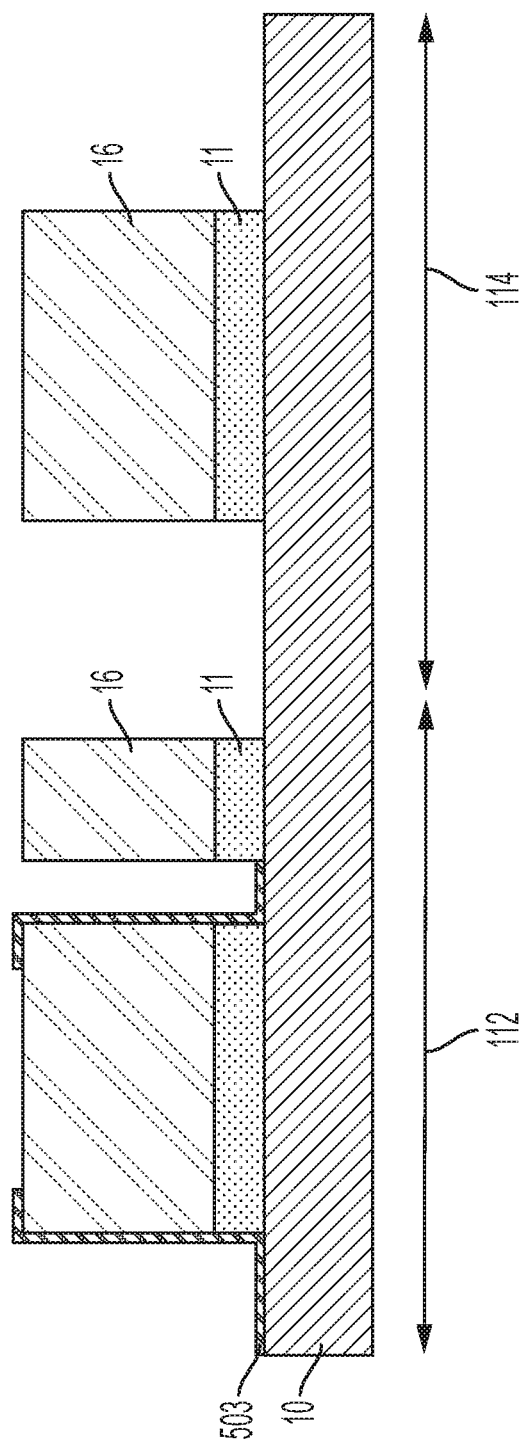
FIG. 9 depicts a cross-sectional view of the integrated optogenetic device after a fabrication stage in accordance with embodiments of the invention.

In FIG. 9, the photo resist pattern 604 has been removed using conventional fabrication techniques.

Figure 10:
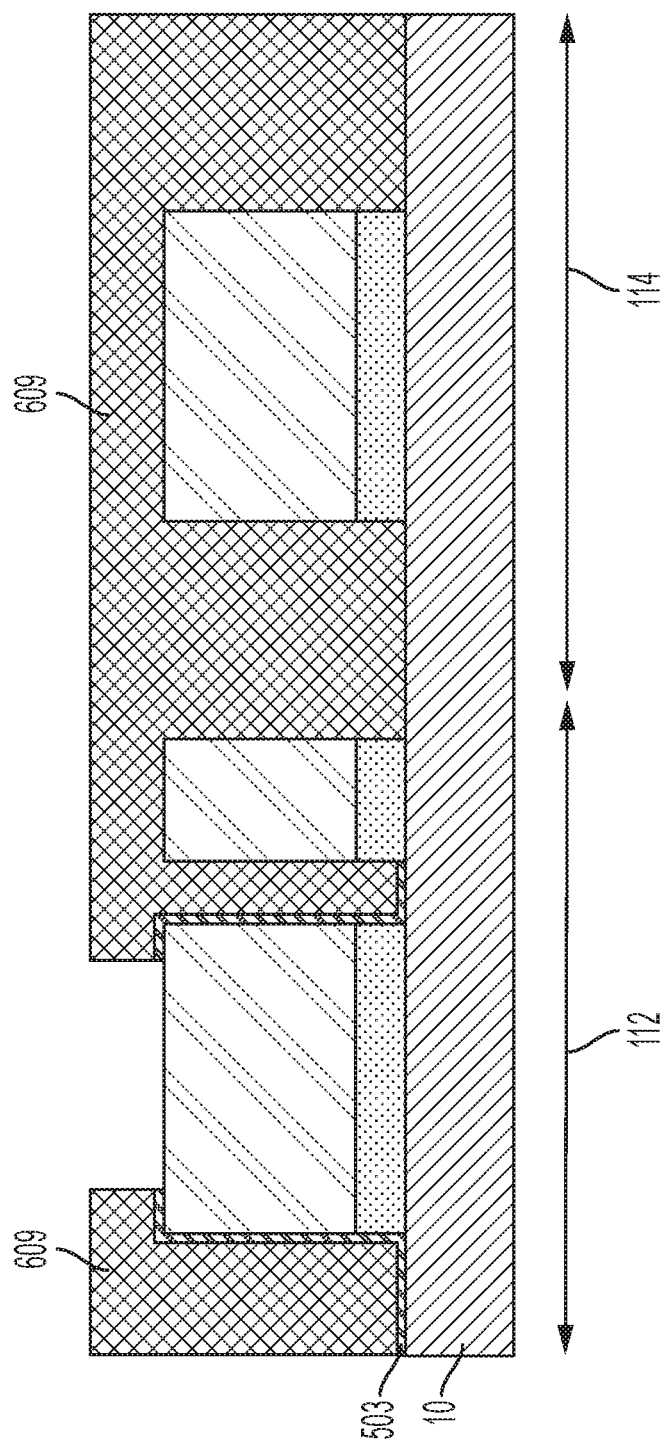
FIG. 10 depicts a cross-sectional view of the integrated optogenetic device after a fabrication stage in accordance with embodiments of the invention.

In FIG. 10, a lithography resist 609 is deposited in order to patter a contact region 102 (shown in FIG. 10) for the LED structure 212 (shown in FIG. 19).

Figure 11:
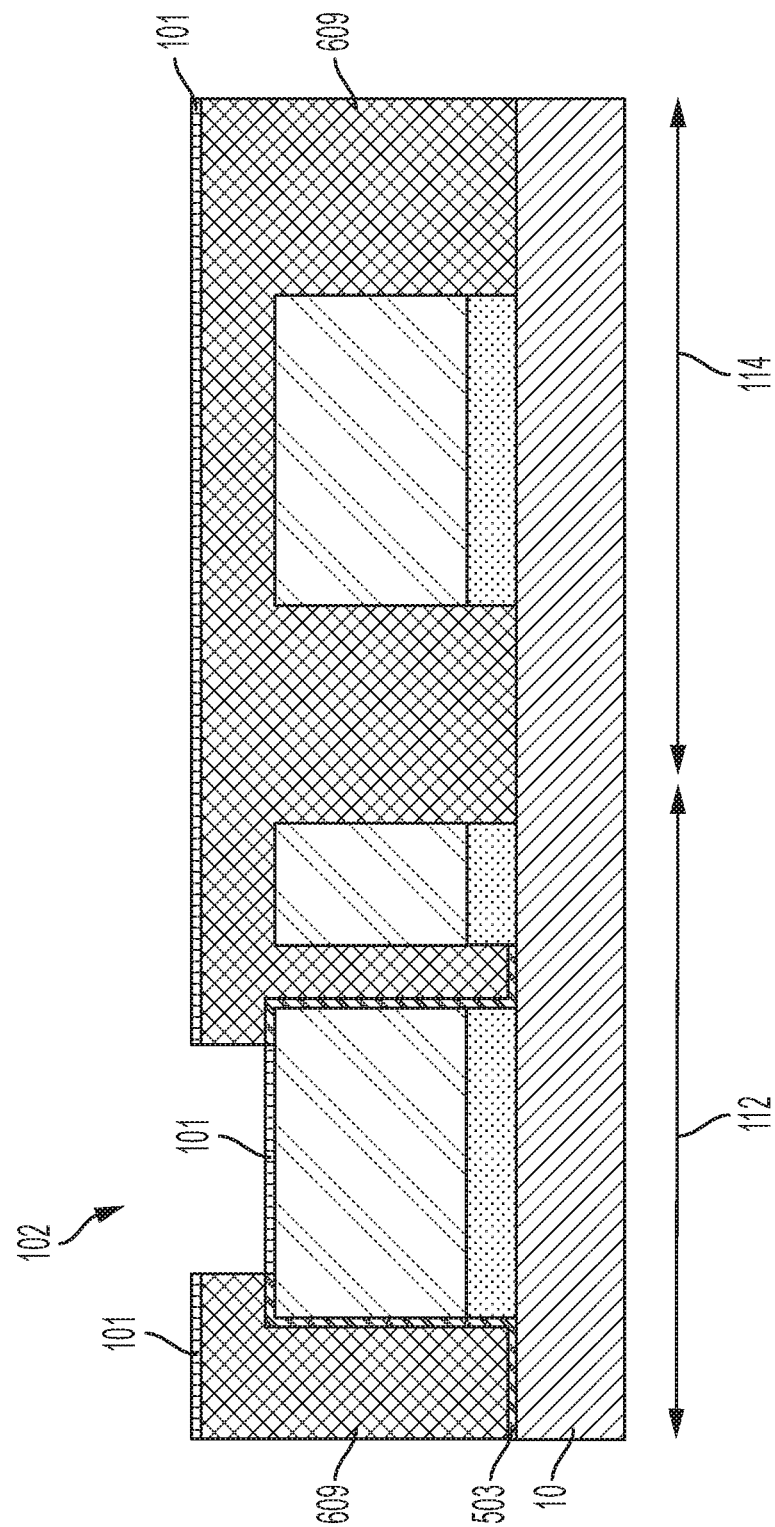
FIG. 11 depicts a cross-sectional view of the integrated optogenetic device after a fabrication stage in accordance with embodiments of the invention.

In FIG. 11, a metal 101 is deposited to form the contact region 102. The metal 101 can be any metal or metal-like element that can react with carbon to form a stable binary metal carbide. Examples of such metals include: Al, Si, Sc, Ti, V, Cr, Mn, Fe, Y, Zr, Nb, Mo, Hf, Ta, W and mixtures or alloys thereof.

Figure 12:
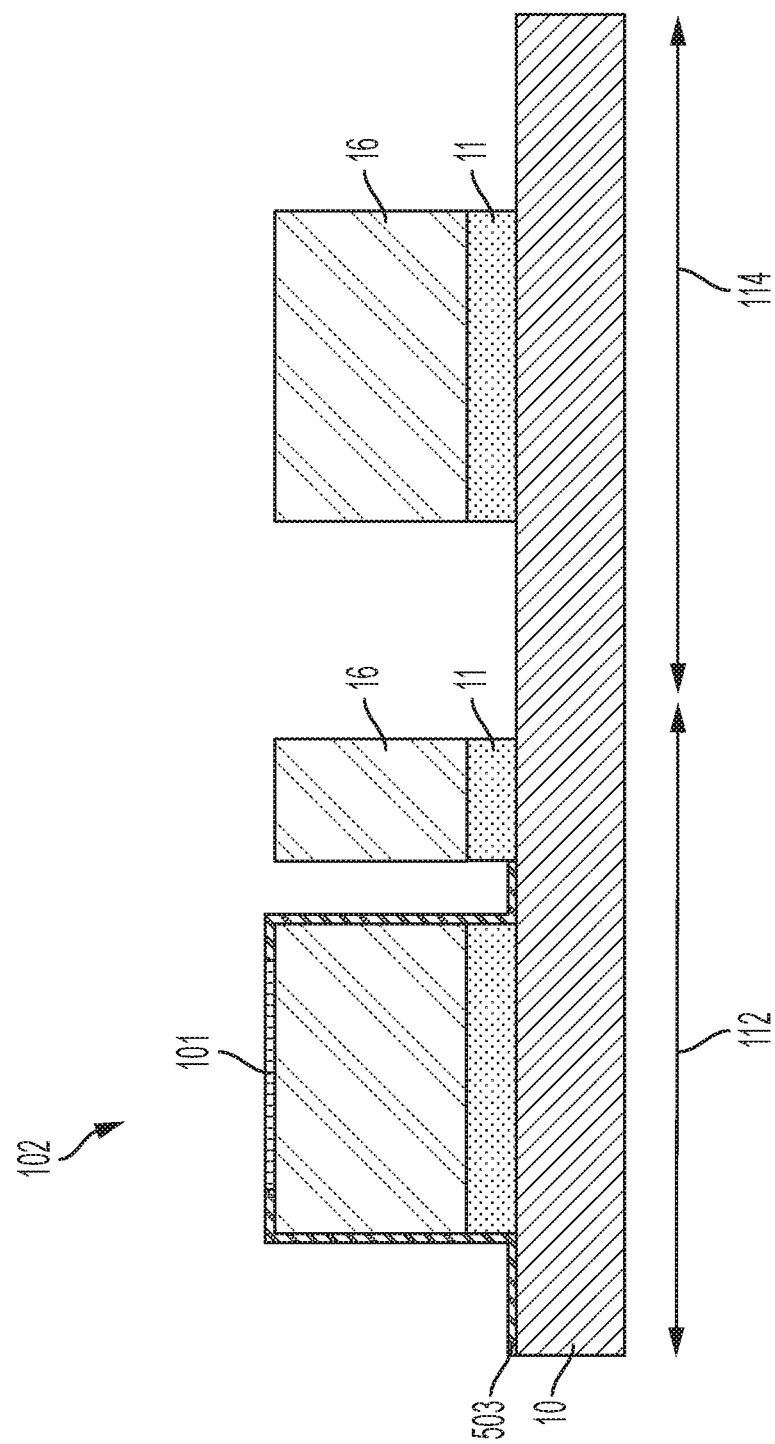
FIG. 12 depicts a cross-sectional view of the integrated optogenetic device after a fabrication stage in accordance with embodiments of the invention.

In FIG. 12, the lithography resist 609 and the metal 101 have been removed using conventional fabrication methods to form the contact region 102.

Figure 13:
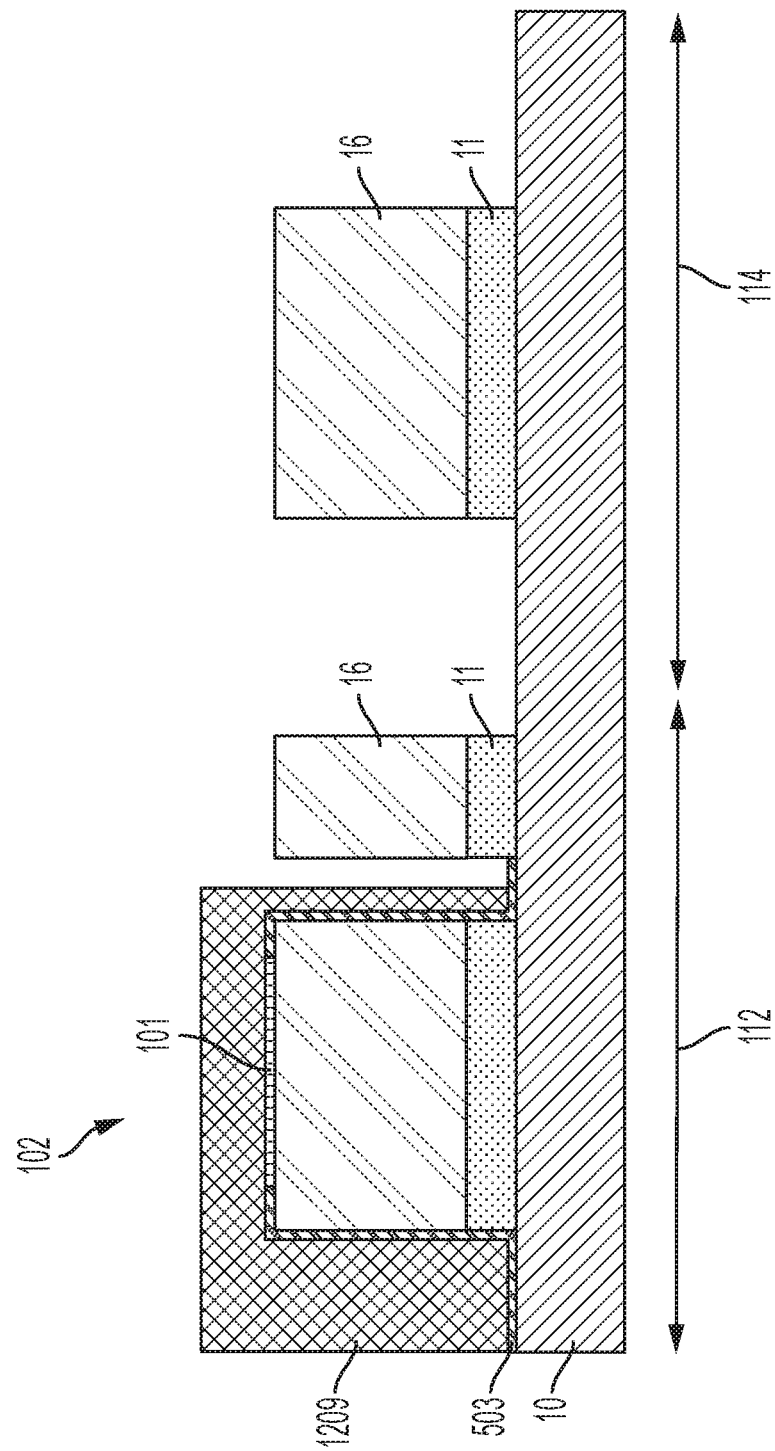
FIG. 13 depicts a cross-sectional view of the integrated optogenetic device after a fabrication stage in accordance with embodiments of the invention.

In FIG. 13, a resist 1209 is deposited to pattern the interconnect network (not shown) including a wire network and pads for the LED structure 212 and the glass-like carbon electrodes of the biosensor element 214.

Figure 14:
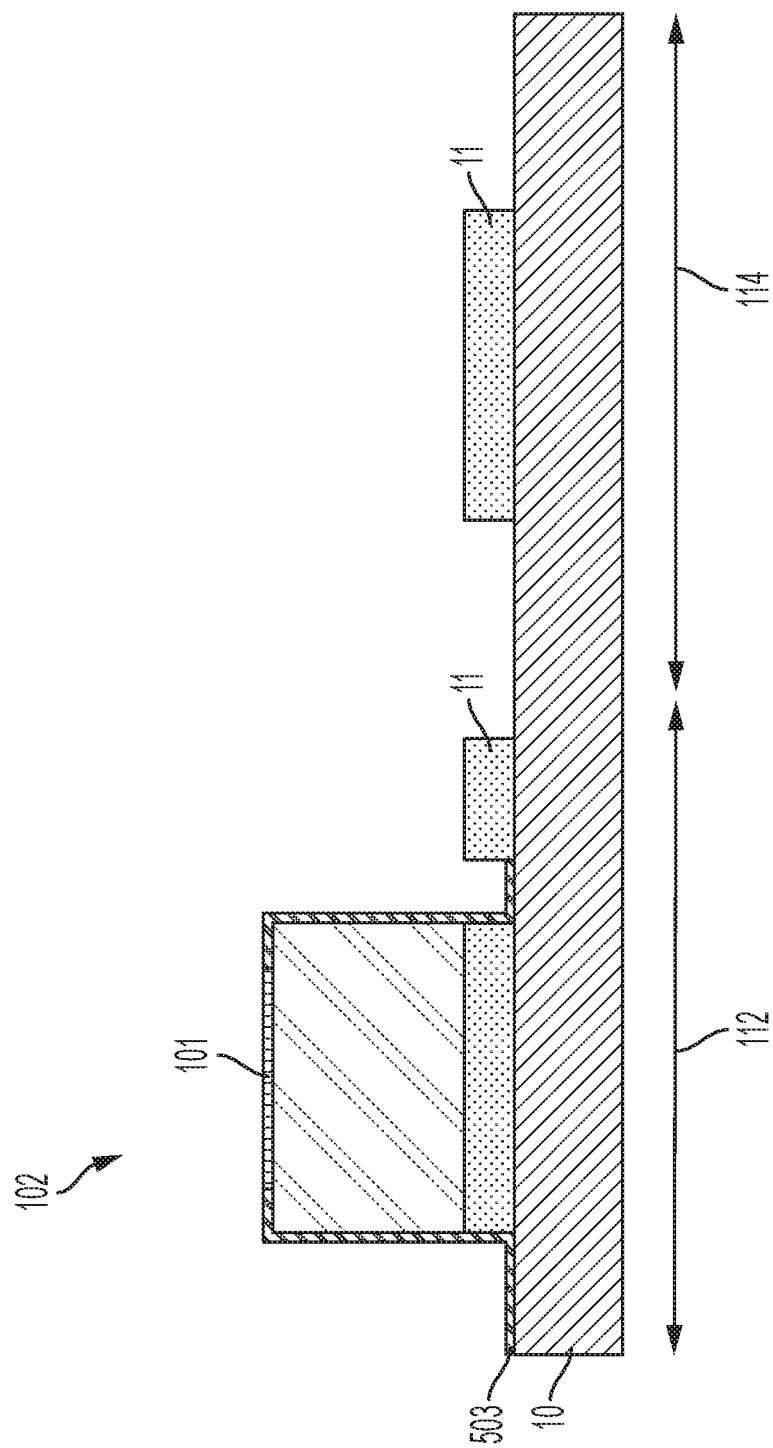
FIG. 14 depicts a cross-sectional view of the integrated optogenetic device after a fabrication stage in accordance with embodiments of the invention.

In FIG. 14, the resist 1209 has been removed using conventional fabrication techniques. The active multilayer stack 16, which includes group III nitride materials, has been removed from the second region 114 using a dry etch (e.g. RIE). Accordingly, the active multilayer stack 16 is only present in the first region 112 and forms the active layers of the LED structure 212.

Figure 15:
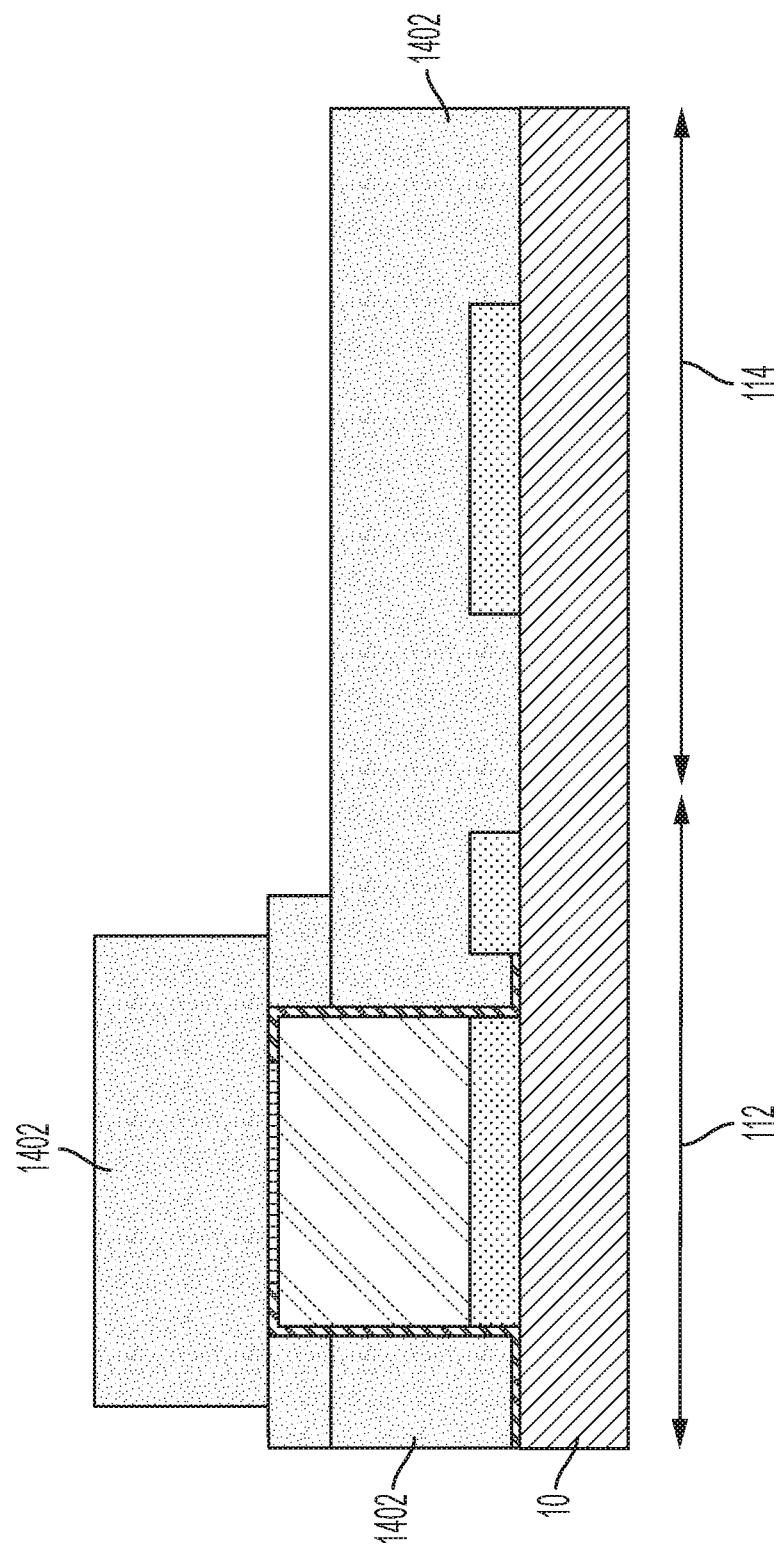
FIG. 15 depicts a cross-sectional view of the integrated optogenetic device after a fabrication stage in accordance with embodiments of the invention.

In FIG. 15, a layer of glass-like carbon 1402 is deposited using conventional fabrication techniques. In embodiments of the invention, the glass-like carbon 1402 is deposited using chemical vapor deposition (CVD). In some embodiments, the CVD process can be a plasma-enhanced CVD (PECVD) process that deposits thin films from a gas state (e.g., a carbon-rich gas species such as methane, ethylene, benzene, and the like) to a solid state (e.g., a carbon-rich polymer) on a substrate (e.g., the substrates 10). Chemical reactions are involved in the PECVD process, which occur after creation of a plasma of the reacting gases. A plasma is any gas in which a significant percentage of the atoms or molecules are ionized. The plasma can be created by radio frequency (RF) or direct current (DC) discharge.

In another embodiment of the invention, the glass-like carbon can be fabricated by using known semiconductor fabrication processes (e.g., spin coating, chemical vapor deposition, lithographic patterning, etching, etc.) to deposit a layer of a glass-like carbon precursor (e.g., a carbon-rich polymer applied as an organic planarization layer (OPL)) on a substrate carrier, and then applying a high temperature anneal (e.g., about 900 Celsius degrees to about 1200 Celsius degrees) to convert the glass-like carbon precursor to a layer of glass-like carbon material.

Figure 16:
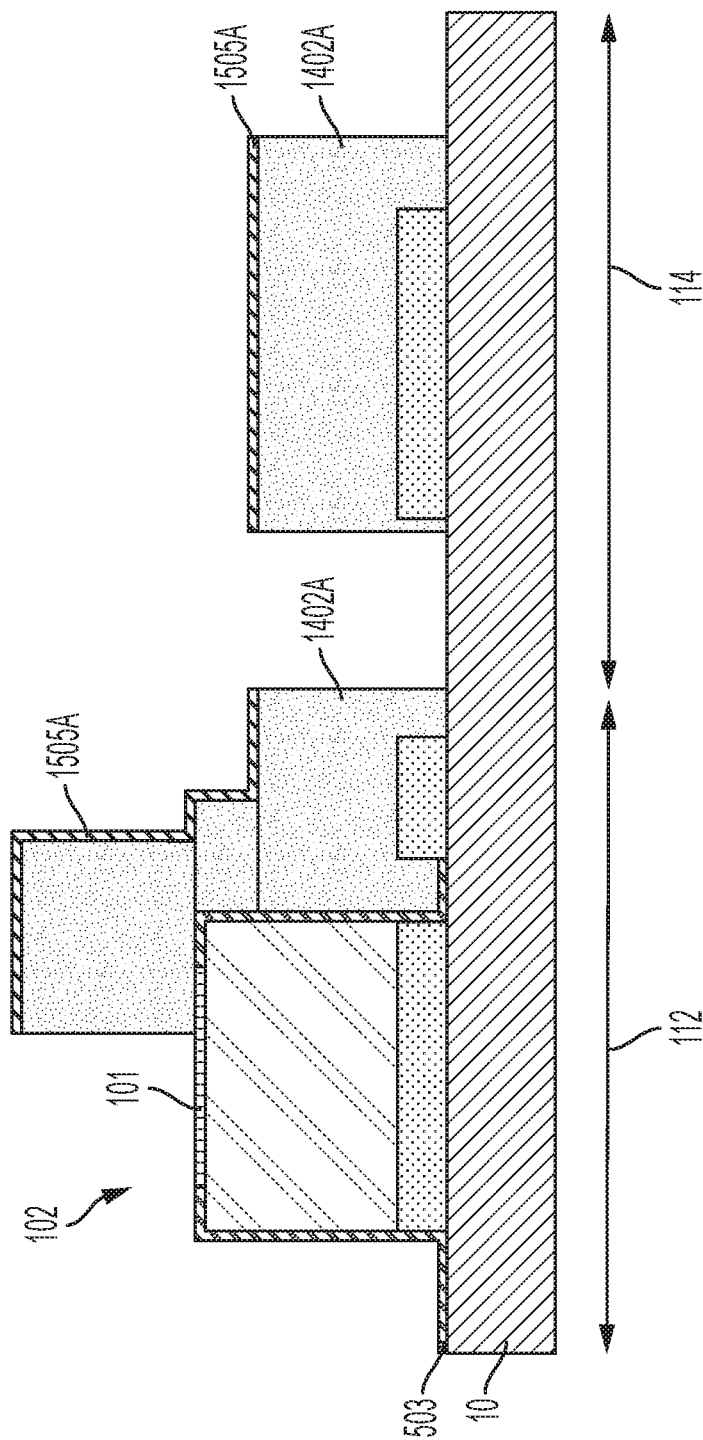
FIG. 16 depicts a cross-sectional view of the integrated optogenetic device after a fabrication stage in accordance with embodiments of the invention.

In FIG. 16, hard mask layer 1505A was formed. In embodiments of the invention, the hard mask layer 1505A can be formed from titanium. The glass-like carbon 1402 has been etched to form the glass-like carbon 1402A. Also, a photo resist pattern (not shown) for defining pillars 1801 (shown in FIG. 18) was deposited.

Figure 17:
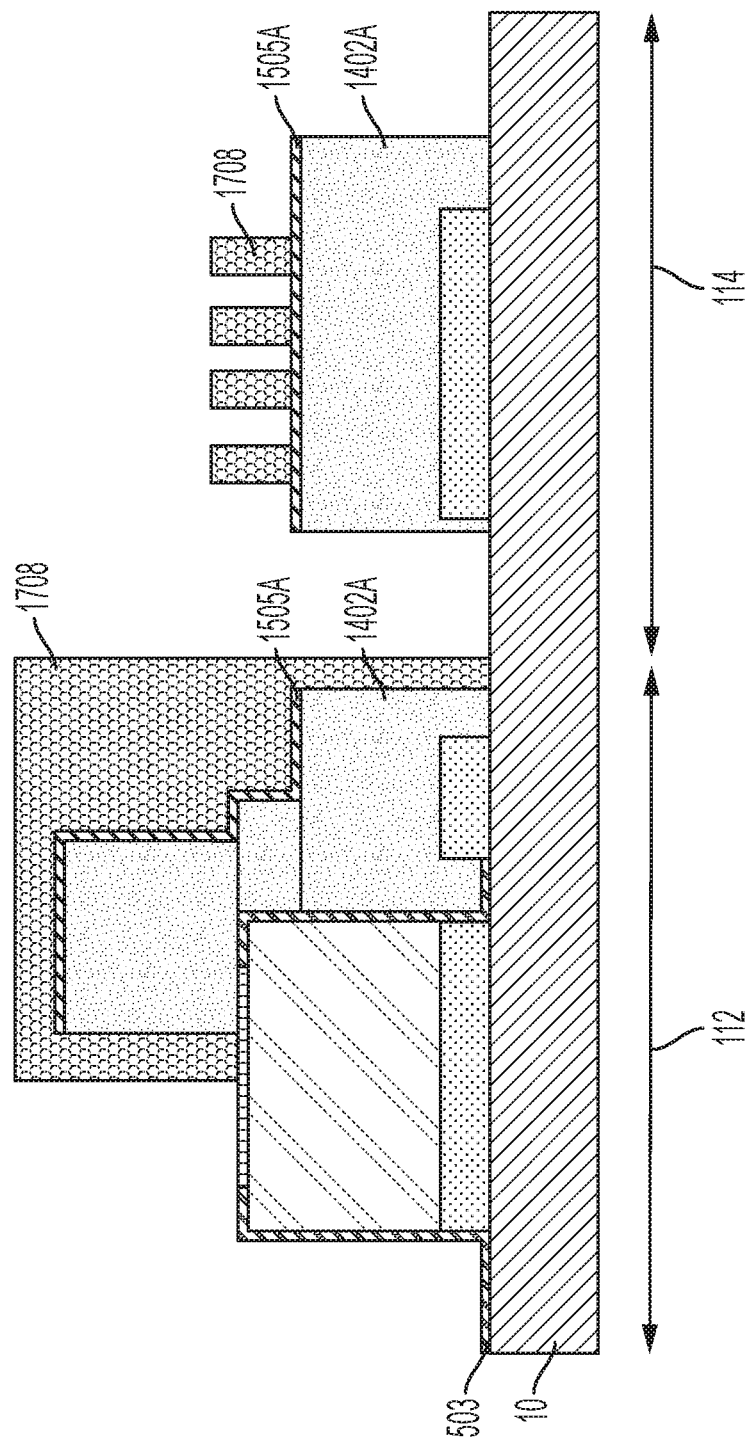
FIG. 17 depicts a cross-sectional view of the integrated optogenetic device after a fabrication stage in accordance with embodiments of the invention.

In FIG. 17, a resist 1708 is deposited to pattern the glass-like carbon pillars 1801 (shown in FIG. 18) in the glass-like carbon 1402A.

In FIG. 18, the resist 1708 has been removed using conventional fabrication techniques. The glass-like carbon 1402A and the hard mask layer 1505A have been etched to form the hard masks 1505B and the glass-like carbon pillars 1801 in the glass-like carbon 1402A in the second region 114.

In FIG. 19, the hard masks 1505A and 1505B have been removed using conventional fabrication techniques (e.g., applying hydrogen peroxide or DHF). A high temperature anneal (e.g., from about 800 Celsius degrees to about 900 Celsius degrees) is applied to the integrated optogenetic device 100 for about one hour. In accordance with embodiments of the invention, each of the pillars 3902 has a height dimension that is less than about 10 microns and a width dimension that is less than about 1 micron.

Figure 20:
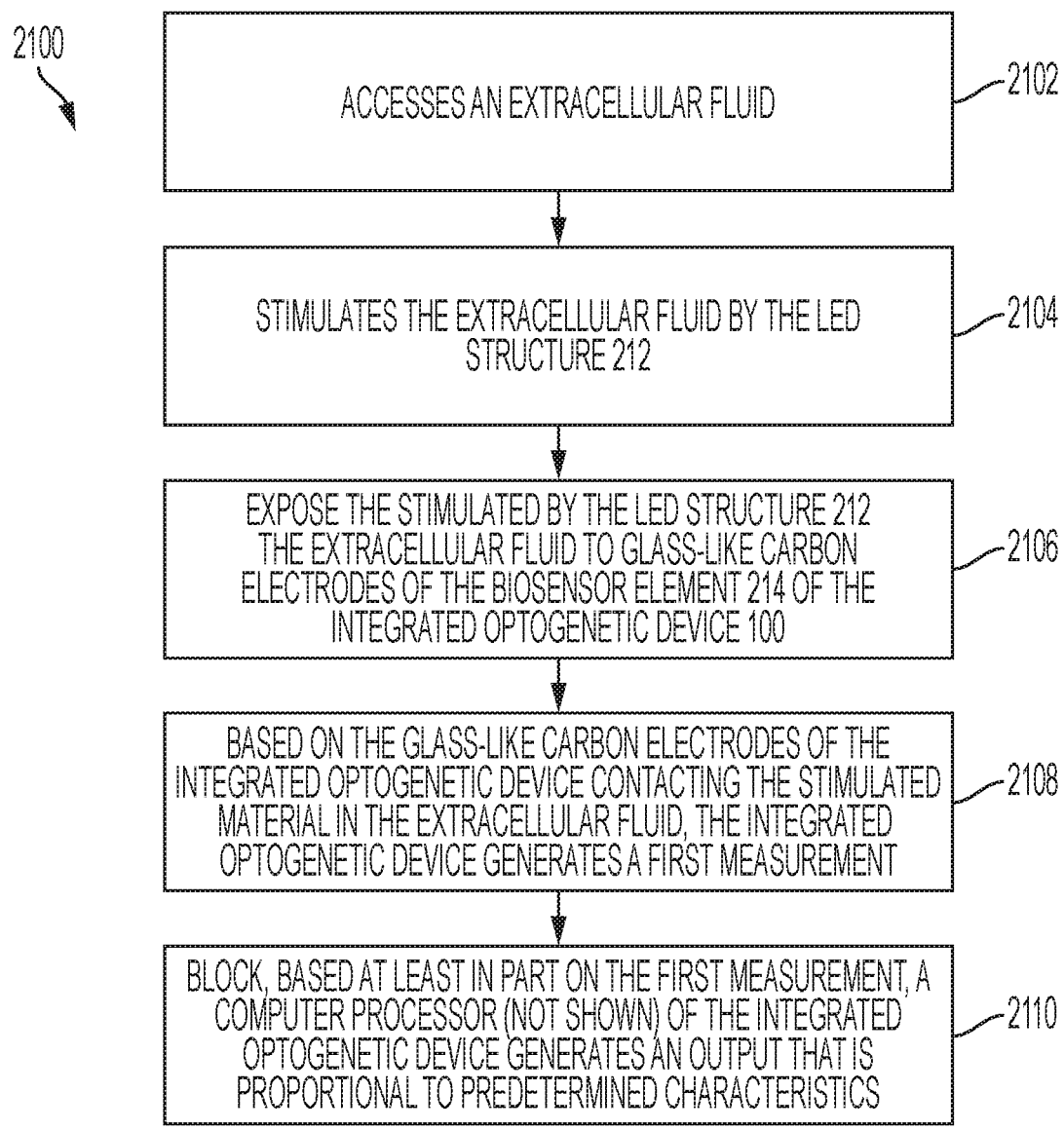
FIG. 20 depicts a flow diagram illustrating a method of using the integrated optogenetic device according to embodiments of the invention.

FIG. 20 is a flow diagram illustrating a method 2100 for using the integrated optogenetic device 100 according to embodiments of the invention. Block 2102 accesses the extracellular fluid (not shown). Block 2104 stimulates the extracellular fluid by the LED structure 212 at an electrode-tissue interface. Block 2106 exposes the stimulated extracellular fluid to glass-like carbon electrodes of the biosensor element 214 of the integrated optogenetic device 100.

In block 2108, based on the glass-like carbon electrodes of the integrated optogenetic device 100 contacting the stimulated material in the extracellular fluid, the integrated optogenetic device generates a measurement. In block 2110, based at least in part on the measurement, a computer processor (not shown) of the integrated optogenetic device generates an output that is proportional to predetermined characteristics.

Methods as described herein can be used in the fabrication of IC chips. The resulting integrated circuit chips can be distributed by the fabricator in raw wafer form (that is, as a single wafer that has multiple unpackaged chips), as a bare die, or in a packaged form. In the latter case, the chip is mounted in a single chip package (e.g., a plastic carrier, with leads that are affixed to a motherboard or other higher level carrier) or in a multichip package (e.g., a ceramic carrier that has either or both surface interconnections or buried interconnections). The chip is then integrated with other chips, discrete circuit elements, and/or other signal processing devices as part of either (a) an intermediate product, such as a motherboard, or (b) an end product.

Various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. As an example of an indirect positional relationship, references in the present description to forming layer "A" over layer "B" include situations in which one or more intermediate layers (e.g., layer "C") is between layer "A" and layer "B" as long as the relevant characteristics and functionalities of layer "A" and layer "B" are not substantially changed by the intermediate layer(s).

As used herein, "semiconductor device" refers to an intrinsic semiconductor material that has been doped, that is, into which a doping agent has been introduced, giving it different electrical properties than the intrinsic semiconductor. Doping involves adding dopant atoms to an intrinsic semiconductor, which changes the electron and hole carrier concentrations of the intrinsic semiconductor at thermal equilibrium. Dominant carrier concentration in an extrinsic semiconductor determines the conductivity type of the semiconductor.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus. Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" are understood to include any integer number greater than or equal to one, i.e. one, two, three, four, etc. The terms "a plurality" are understood to include any integer number greater than or equal to two, i.e. two, three, four, five, etc. The term "connection" can include an indirect "connection" and a direct "connection."

References in the specification to "one embodiment," "an embodiment," "an example embodiment," etc., indicate that the embodiment described can include a particular feature, structure, or characteristic, but every embodiment may or may not include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

For purposes of the description hereinafter, the terms "upper," "lower," "right," "left," "vertical," "horizontal," "top," "bottom," and derivatives thereof shall relate to the described structures and methods, as oriented in the drawing figures. The terms "overlying," "atop," "on top," "positioned on" or "positioned atop" mean that a first element, such as a first structure, is present on a second element, such as a second structure, wherein intervening elements such as an interface structure can be present between the first element and the second element. The term "direct contact" means that a first element, such as a first structure, and a second element, such as a second structure, are connected without any intermediary conducting, insulating or semiconductor layers at the interface of the two elements.

Spatially relative terms, e.g., "beneath," "below," "lower," "above," "upper," and the like, are used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" can encompass both an orientation of above and below. The device can be otherwise oriented (e.g., rotated 90 degrees or at other orientations), and the spatially relative descriptors used herein should be interpreted accordingly.

The terms "epitaxial growth and/or deposition" and "epitaxially formed and/or grown" mean the growth of a semiconductor material (crystalline material) on a deposition surface of another semiconductor material (crystalline material), in which the semiconductor material being grown (crystalline overlayer) has substantially the same crystalline characteristics as the semiconductor material of the deposition surface (seed material). In an epitaxial deposition process, the chemical reactants provided by the source gases can be controlled and the system parameters can be set so that the depositing atoms arrive at the deposition surface of the semiconductor substrate with sufficient energy to move about on the surface such that the depositing atoms orient themselves to the crystal arrangement of the atoms of the deposition surface. An epitaxially grown semiconductor material can have substantially the same crystalline characteristics as the deposition surface on which the epitaxially grown material is formed. For example, an epitaxially grown semiconductor material deposited on a (100) orientated crystalline surface can take on a (100) orientation. In some embodiments of the invention, epitaxial growth and/or deposition processes can be selective to forming on semiconductor surface, and cannot deposit material on exposed surfaces, such as silicon dioxide or silicon nitride surfaces.

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

The phrase "selective to," such as, for example, "a first element selective to a second element," means that the first element can be etched and the second element can act as an etch stop.

The term "conformal" (e.g., a conformal layer) means that the thickness of the layer is substantially the same on all surfaces, or that the thickness variation is less than 15% of the nominal thickness of the layer.

As previously noted herein, for the sake of brevity, conventional techniques related to semiconductor device and integrated circuit (IC) fabrication may or may not be described in detail herein. By way of background, however, a more general description of the semiconductor device fabrication processes that can be utilized in implementing one or more embodiments of the present invention will now be provided. Although specific fabrication operations used in implementing one or more embodiments of the present invention can be individually known, the described combination of operations and/or resulting structures of the present invention are unique. Thus, the unique combination of the operations described in connection with the fabrication of a semiconductor device according to the present invention utilize a variety of individually known physical and chemical processes performed on a semiconductor (e.g., silicon) substrate, some of which are described in the immediately following paragraphs.

In general, the various processes used to form a microchip that will be packaged into an IC fall into four general categories, namely, film deposition, removal/etching, semiconductor doping and patterning/lithography. Deposition is any process that grows, coats, or otherwise transfers a material onto the wafer. Available technologies include physical vapor deposition (PVD), chemical vapor deposition (CVD), electrochemical deposition (ECD), molecular beam epitaxy (MBE) and more recently, atomic layer deposition (ALD) among others. Removal/etching is any process that removes material from the wafer. Examples include etch processes (either wet or dry), chemical-mechanical planarization (CMP), and the like. Reactive ion etching (RIE), for example, is a type of dry etching that uses chemically reactive plasma to remove a material, such as a masked pattern of semiconductor material, by exposing the material to a bombardment of ions that dislodge portions of the material from the exposed surface. The plasma is typically generated under low pressure (vacuum) by an electromagnetic field. Semiconductor doping is the modification of electrical properties by doping, for example, transistor sources and drains, generally by diffusion and/or by ion implantation. These doping processes are followed by furnace annealing or by rapid thermal annealing (RTA). Annealing serves to activate the implanted dopants. Films of both conductors (e.g., poly-silicon, aluminum, copper, etc.) and insulators (e.g., various forms of silicon dioxide, silicon nitride, etc.) are used to connect and isolate transistors and their components. Selective doping of various regions of the semiconductor substrate allows the conductivity of the substrate to be changed with the application of voltage. By creating structures of these various components, millions of transistors can be built and wired together to form the complex circuitry of a modern microelectronic device. Semiconductor lithography is the formation of three-dimensional relief images or patterns on the semiconductor substrate for subsequent transfer of the pattern to the substrate. In semiconductor lithography, the patterns are formed by a light sensitive polymer called a photo-resist. To build the complex structures that make up a transistor and the many wires that connect the millions of transistors of a circuit, lithography and etch pattern transfer steps are repeated multiple times. Each pattern being printed on the wafer is aligned to the previously formed patterns and slowly the conductors, insulators and selectively doped regions are built up to form the final device.

The flowchart and block diagrams in the Figures illustrate possible implementations of fabrication and/or operation methods according to various embodiments of the present invention. Various functions/operations of the method are represented in the flow diagram by blocks. In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved.

The descriptions of the various embodiments of the present invention have been presented for purposes of illustration, but are not intended to be exhaustive or limited to the embodiments described. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A method of forming an integrated optogenetic device, the method comprising:
    forming a substrate layer, wherein the substrate layer comprises a first substrate region and a second substrate region;
    forming a first contact layer over the substrate layer in the first substrate region;
    forming a second contact layer over the substrate layer in the second substrate region;
    forming a light-emitting diode (LED) structure communicatively coupled to the first contact layer, the LED structure comprising an active layer directly on a first portion of the first contact layer, a dielectric layer that covers sidewalls of the active layer and sidewalls of the first portion of the first contact layer, and a conductive layer positioned on a top surface of the active layer, wherein a glassy-carbon region electrically couples the conductive layer to a second portion of the first contact layer; and
    forming a biosensor element communicatively coupled to the second contact layer, the biosensor element comprising at least one pillar-shaped electrode body comprising a glass-like carbon material.

2. The method of claim 1 further comprising forming an active layer communicatively coupled to the first contact layer in the first substrate region.

3. The method of claim 1 wherein the first contact layer and the second contact layer comprise $ZrB_2$.

4. The method of claim 2, wherein the active layer is substantially lattice matched with the first contact layer.

5. The method of claim 4, wherein the active layer comprises a group III nitride materials, selected from the group consisting of gallium nitride (GaN), aluminum nitride (AlN), aluminum nitride (InN), and their alloys such as aluminum gallium nitride (AlGaN), indium gallium nitride (InGaN), and aluminum indium gallium nitride (AlInGaN).

6. The method of claim 1, wherein forming the biosensor element comprises:
    forming over the second substrate region a layer of a glass-like carbon material; and
    removing portions of the layer of the glass-like carbon material to form the at least one pillar.

7. The method of claim 1, wherein the first contact layer and the second contact layer each comprises a compound having formula $XB_2$, where X is zirconium (Zr) or titanium (Ti).

8. The method of claim 1, wherein the LED structure comprises a plurality of LEDs configured to generate data based on optical parameters.

* * * * *